United States Patent
Yerebakan et al.

(10) Patent No.: US 12,288,609 B2
(45) Date of Patent: Apr. 29, 2025

(54) IMAGE RETRIEVAL

(71) Applicant: Siemens Healthineers AG, Forchheim (DE)

(72) Inventors: Halid Yerebakan, Carmel, IN (US); Yoshihisa Shinagawa, Downingtown, PA (US); Anna Jerebko, Lexington, MA (US)

(73) Assignee: Siemens Healthineers AG, Forchheim (DE)

(\*) Notice: Subject to any disclaimer, the term of this patent is extended or adjusted under 35 U.S.C. 154(b) by 428 days.

(21) Appl. No.: 17/236,273

(22) Filed: Apr. 21, 2021

(65) Prior Publication Data

US 2021/0358600 A1    Nov. 18, 2021

(30) Foreign Application Priority Data

May 13, 2020 (EP) .................................... 20174500

(51) Int. Cl.
| | | |
|---|---|---|
| G06F 16/58 | (2019.01) | |
| G06T 7/00 | (2017.01) | |
| G16H 30/40 | (2018.01) | |

(52) U.S. Cl.
CPC ......... *G16H 30/40* (2018.01); *G06F 16/5866* (2019.01); *G06T 7/0014* (2013.01);
(Continued)

(58) Field of Classification Search
None
See application file for complete search history.

(56) References Cited

U.S. PATENT DOCUMENTS

2013/0230237 A1\* 9/2013 Schlosser ............... G06T 7/194
                                                                382/164
2019/0065688 A1\* 2/2019 Lee ........................ G06Q 50/22
(Continued)

FOREIGN PATENT DOCUMENTS

| CN | 101765843 A | 6/2010 |
|---|---|---|
| CN | 102473182 A | 5/2012 |

(Continued)

OTHER PUBLICATIONS

Wu Meng-Sung et al; "A Term Association Translation Model for Naive Bayes Text Classification"; May 29, 2012 (May 29, 2012); Advances in Knowledge Discovery and Data Mining; Springer Berlin Heidelberg; Berlin; Heidelberg; pp. 243-253.
(Continued)

*Primary Examiner* — Giuseppi Giuliani

(57) ABSTRACT

Method and apparatus for image retrieval. An image descriptor of a query image indicating a medical abnormality and non-image patient data may be received. For each of a plurality of candidate images stored in a database, an image descriptor of the candidate image and data about a medical abnormality known to be indicated by the candidate image may further be received. A similarity metric between the image descriptors of the query image and the candidate image may be determined for each candidate image. A first probability of the query image medical abnormality being the candidate image medical abnormality given the non-image patient data associated with the query image may be determined for each candidate image. A score may then be determined for each candidate image based on the determined similarity metric and the determined first probability. One or more of the candidate images may be retrieved from the database in accordance with the determined scores.

20 Claims, 3 Drawing Sheets

(52) U.S. Cl.
 CPC ............... *G06T 2207/20076* (2013.01); *G06T 2207/30004* (2013.01); *G06V 2201/03* (2022.01)

(56) References Cited

U.S. PATENT DOCUMENTS

2020/0161005 A1* 5/2020 Lyman .................... G06N 5/04
2021/0019342 A1* 1/2021 Peng ................. G06F 16/5854

FOREIGN PATENT DOCUMENTS

| CN | 105359161 A | 2/2016 |
|---|---|---|
| CN | 106233322 A | 12/2016 |
| WO | 2007082218 A2 | 7/2007 |
| WO | 2013119400 A1 | 8/2013 |
| WO | 2014139021 A1 | 9/2014 |
| WO | 2017124116 A1 | 7/2017 |
| WO | 2020013814 A1 | 1/2020 |

OTHER PUBLICATIONS

Dong Yuning; "Medical Image Processing Theories and Applications"; Medical Image Processing Theories and Applications; Aug. 31, 2020; Southeast University Press, English translation attached.

\* cited by examiner

IMAGE RETRIEVAL

TECHNICAL FIELD

The present disclosure relates to image retrieval.

BACKGROUND

A radiologist reads a medical image of a patient to consider whether it shows the presence of a particular medical abnormality, such as a disease.

In considering a possible diagnosis, a radiologist may consider different medical abnormalities that present similarly to as shown in the medical image of the patient. To aid this process, the radiologist may look (e.g. in medical text books) for similar prior medical images for each of which the medical abnormality is known. This may help the radiologist to decide whether or not the current medical image does or does not indicate the presence of a particular medical abnormality.

A computer implemented retrieval of prior medical images for each of which the medical abnormality is known and which are similar or relevant to a query medical image is therefore desirable to aid the diagnosis process.

SUMMARY

According to one aspect, there is provided a computer implemented image retrieval method comprising: receiving an image descriptor of a query image and non-image patient data associated with the query image, the query image indicating a medical abnormality; receiving, for each of a plurality of candidate images stored in a database, an image descriptor of the candidate image and medical abnormality data indicating a medical abnormality known to be indicated by the candidate image; determining, for each of the plurality of candidate images, a similarity metric representing a similarity between the image descriptor of the query image and the image descriptor of the candidate image; determining, for each of the plurality of candidate images, a first probability of the medical abnormality indicated by the query image being the medical abnormality known to be indicated by the candidate image given the non-image patient data associated with the query image; determining, for each of the plurality of candidate images, based on the determined similarity metric and the determined first probability, a score; and retrieving one or more of the candidate images from the database in accordance with the determined scores.

DETAILED DESCRIPTION

Figure 1:
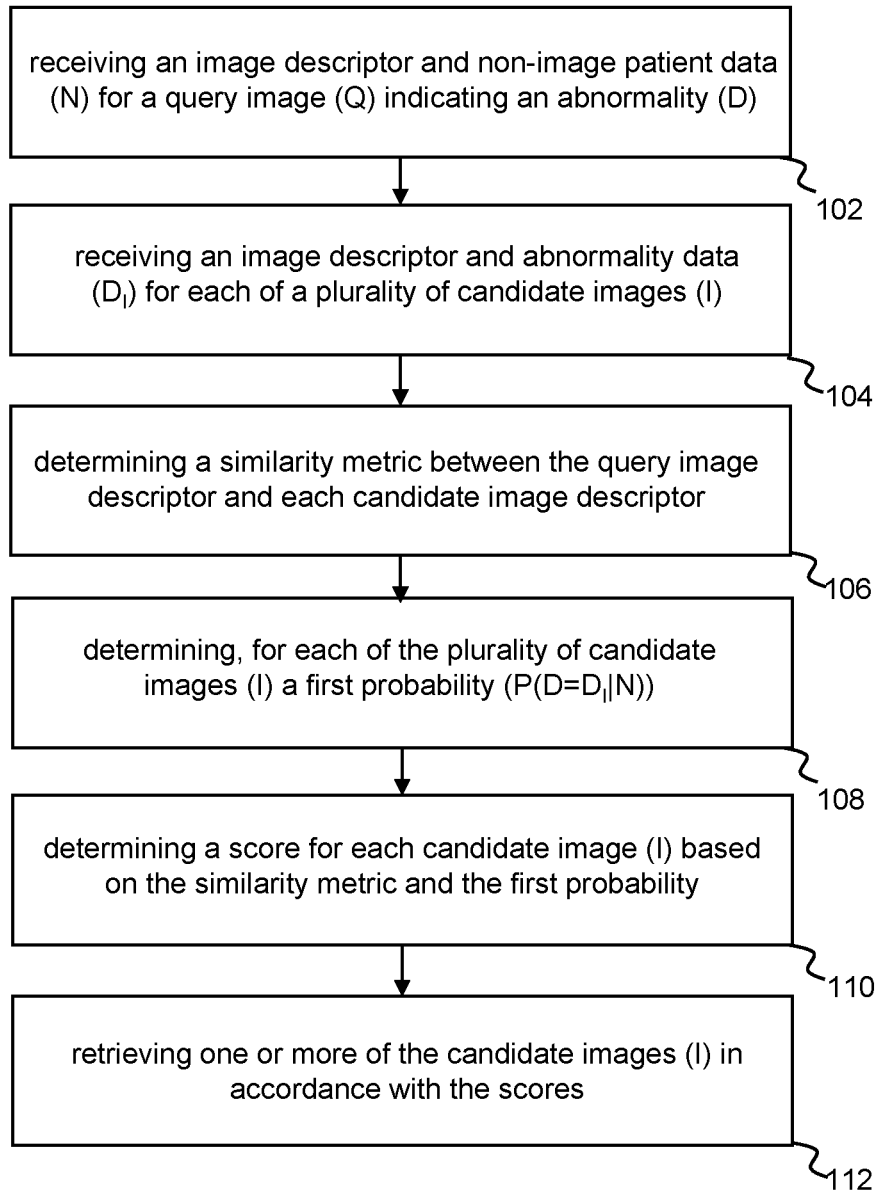
FIG. 1 is a flow diagram illustrating schematically a method according to an example.

Referring to FIG. 1, there is illustrated a computer implemented image retrieval method. In broad overview, the method includes:

in step 102, receiving an image descriptor of a query image Q and non-image patient data N associated with the query image Q, the query image Q indicating a medical abnormality D;

in step 104, receiving, for each of a plurality of candidate images I stored in a database, an image descriptor of the candidate image I and medical abnormality data indicating a medical abnormality $D_I$ known to be indicated by the candidate image I;

in step 106, determining, for each of the plurality of candidate images I, a similarity metric representing a similarity between the image descriptor of the query image Q and the image descriptor of the candidate image I;

in step 108, determining, for each of the plurality of candidate images I a first probability $P(D=D_I|N)$ of the medical abnormality D indicated by the query image Q being the medical abnormality $D_I$ known to be indicated by the candidate image I given the non-image patient data N associated with the query image Q;

in step 110, determining, for each of the plurality of candidate images I, based on the determined similarity metric and the determined first probability $P(D=D_I|N)$, a score; and in step 112, retrieving one or more of the candidate images I from the database in accordance with the determined scores.

Accordingly, non-image patient data N, such as specific demographics of the patient, are incorporated into a scoring of the relevance of candidate images I to a query image Q, and hence into the retrieval of candidate images I from the database. That is, candidate images I are retrieved from a database not only based on the similarity of the image descriptors of the query image Q and the previous images I for which the medical abnormality is known, but also non-image patient data N associated with the patient of the query image Q. This may allow for candidate images I to be retrieved which are more relevant to the query image Q (i.e. more likely to indicate the same medical abnormality as the query image Q), for example as compared to if the score was based on the similarity of image descriptors alone.

The inventors have realized that the relevance of a candidate image I indicating a known medical abnormality $D_I$ to the query image Q is influenced by the probability of that medical abnormality $D_I$ occurring in a patient having the non-image patient data N of the patient of the query image Q, and that this can be effectively determined and incorporated into a relevance score, for example using Bayesian inference. This probability can be based on real-world and/or empirical observations of medical abnormality prevalence given non-image patient data, such as gender, age, and/or smoking status and the like. Using this score to retrieve candidate images I allows for candidate images I to be retrieved which are more relevant to the query image Q (i.e. more likely to indicate the same medical abnormality as the query image Q), for example as compared to if the score was based on the similarity of image descriptors alone. This may, in turn, allow a radiologist to be presented with candidate images I, for which the medical abnormality is known, that are more relevant to the query image Q. This may allow for a precise and efficient diagnosis of the medical abnormality indicated in the query image Q.

In other words, through the incorporation of the non-image patient data into the image retrieval process, certain medical abnormalities can be disambiguated automatically as part of the image retrieval process. This may improve the relevance of the candidate images retrieved, and in turn the efficiency of the diagnostic process.

Moreover, the improved relevance of the retrieved images I is provided for by incorporating into the score the first probability $P(D=D_I|N)$ which encapsulates the natural phenomenon of certain medical abnormalities such as diseases being linked to (i.e. having particular prevalence in) certain non-image patient data such as age, gender, and the like. For example, this first probability can be based on real-world and/or empirical observations of medical abnormality prevalence given non-image patient data. The improved relevance of the retrieved candidate images I is therefore based on an encapsulation of natural phenomena occurring in the medical field, therefore providing an objective basis on which the relevance is improved.

As mentioned, in step 102, the method includes receiving an image descriptor of a query image Q and non-image patient data N associated with the query image Q, the query image Q indicating a medical abnormality D.

In some examples, the query image Q may be a medical scan, such as a Computed Tomography (CT) scan or a Magnetic Resonance Imaging (MRI) scan, or an X-ray image, or the like.

The medical abnormality D indicated by the query image Q may be a medical abnormality D to be identified or diagnosed, for example by a radiologist or another medical practitioner. In some examples, the medical abnormality D may be a disease. The query image Q may show a manifestation of a disease thereby indicating the disease. In some examples, the medical abnormality may be an injury. The query image Q may show a manifestation of the injury thereby indicating the injury. For example, the query image Q may show a lesion, i.e. a region in an organ or tissue which has suffered damage through injury or disease, such as a wound, ulcer, abscess, or tumor.

In some examples, the image descriptor may be a vector representing or characterizing the query image Q in a particular vector space. In some examples, the image descriptor may be determined by encoding the query image Q using a particular image descriptor encoding algorithm. Features of the query image Q, such as the manifestation of the medical abnormality indicated by the query image Q, are represented or characterized by the image descriptor.

The non-image patient data N associated with the query image Q is data of the patient who is the subject of the query image Q. The non-image patient data N may include, for example, one or both of demographic data and clinical data of the patient. For example, the non-image patient data N may include one or more of the age, gender, smoking status and clinical status of the patient. For example, clinical status of the patient may include clinical symptoms of the patient and/or clinical data such as blood pressure and/or pre-existing medical conditions.

In some examples, the non-image patient data N associated with the query image Q may be obtained or derived from header information of the query image Q itself. For example, the query image Q may include a DICOM (Digital Imaging and Communications in Medicine) header including patient information such as age and gender, and parts or all of this patient information may be extracted from the header to form the non-image patient data.

In some examples, the image descriptor of the query image Q and the non-image patient data associated with the query image Q may be received from an input terminal, for example over wired or wireless communication channels, and/or may be extracted from a memory of a computing device.

In some examples, a radiologist may specify a query image Q, and the computer implemented method may include determining the image descriptor for the query image Q (for example by running an appropriate encoding algorithm or by extracting a pre-determined image descriptor associated with the image from a memory) and determining the non-image patient data (for example by extracting non-image patient data from a header of the image and/or from a memory storing the non-image patient data).

As mentioned, in step 104, the method includes receiving, for each of a plurality of candidate images I stored in a database, an image descriptor of the candidate image I and medical abnormality data indicating a medical abnormality $D_I$ known to be indicated by the candidate image I.

For example, a database may store candidate images I, for example hundreds or thousands of candidate images I, each in association with an image descriptor of the candidate image, and data indicating the medical abnormality known to be indicated by the candidate image I. For example, the medical abnormality may be as identified or diagnosed by a medical practitioner. The medical abnormality may be a disease or an injury. The candidate image I may show a manifestation of the medical abnormality, such as a disease or injury, thereby indicating the medical abnormality. The medical abnormality data associated with a given candidate image I may include the name of the medical abnormality, such as the name of the disease or injury, known to be indicated in the given candidate image (e.g. as previously determined by a medical professional). The image descriptor of each candidate image I may be a vector representing or characterizing the candidate image I in a particular vector space, for example in the same vector space in which the image descriptor of the query image Q is represented. For each candidate image I, features of the candidate image, such as the manifestation of the medical abnormality indicated by the candidate image I, are represented or characterized by the image descriptor. The medical abnormality data and the image descriptor of each candidate image I may be extracted from the database. In some examples, the database may be a medical records database of a hospital or the like.

It will be appreciated that in some examples, the plurality of candidate images I for each of which the image descriptor and the medical abnormality data are received may represent a subset or only some of the candidate images I stored in the database. In other words, the method described herein need not be applied for each and every one of the candidate images I stored in the database, and in some examples may be applied for less than all of the candidate images I stored in the database.

As mentioned, in step 106, the method includes determining, for each of the plurality of candidate images I, a similarity metric representing a similarity between the image descriptor of the query image Q and the image descriptor of the candidate image I.

In some examples, the similarity metric may be a distance in vector space between the image descriptor of the query image Q and the image descriptor of the candidate image I. For example, the distance may be the Euclidean distance between the two points in vector space that the candidate and query image descriptors represent. For example, if q represents the vector of the query image and i represents the vector of the candidate image, the distance between the vectors may be calculated as $\|q-i\|^2$. In some examples, the similarity metric may be the $L_1$ norm of the candidate image descriptor vector and the query image descriptor vector. In some examples, other similarity metrics may be used, such as a cosine similarity between the image descriptor (e.g. vector) of the query image Q and the image descriptor (e.g. vector) of the candidate image I. For each candidate image I, the similarity metric may represent how visually similar the candidate image is to the query image Q.

As mentioned, in step 108, the method includes determining, for each of the plurality of candidate images I a first probability $P(D=D_I|N)$ of the medical abnormality D indicated by the query image Q being the medical abnormality $D_I$ known to be indicated by the candidate image I given the non-image patient data N associated with the query image Q. For example, the first probability $P(D=D_I|N)$ may be determined using Bayesian inference.

In some examples, for each of the plurality of candidate images I, the first probability $P(D=D_I|N)$ may be determined based on a first likelihood $P(N|D=D_I)$ of observing the non-image patient data N given the medical abnormality $D_I$ known to be indicated by the candidate image I. For example, the first likelihood $P(N|D=D_I)$ may be determined from first distribution data representing a first distribution of the medical abnormality $D_I$ known to be indicated by the candidate image I among said non-image patient data of a population of patients. For example, the first distribution may have been derived empirically.

In some examples, for each of the plurality of candidate images I, the first probability ($P(D=D_I|N)$) may be determined based on a second probability ($P(D=D_I)$) of observing the medical abnormality ($D_I$) known to be indicated by the candidate image (I) among other medical abnormalities.

For example, according to Bayesian inference or calculation, the first probability $P(D=D_I|N)$ of the medical abnormality D indicated by the query image Q being the medical abnormality $D_I$ known to be indicated by the candidate image I given the non-image patient data N associated with the query image Q, may be calculated as:

$$P(D = D_I | N) = \frac{P(N | D = D_I)P(D = D_I)}{P(N)} \quad (1)$$

where $P(N|D=D_I)$ is the likelihood of observing the non-image patient data N given the medical abnormality $D_I$ known to be indicated by the candidate image I; $P(D=D_I)$ is the general probability of the occurrence of the medical abnormality ($D_I$) known to be indicated by the candidate image (I) among medical abnormalities; and P(N) is the marginal likelihood of observing the non-image patient data N among other non-image patient data.

The marginal likelihood P(N) is a normalization term, and is the same in the calculation for all candidate images I. This term may therefore be ignored for the purposes of determining of a relative score for each of the candidate images I. In some examples, this term is ignored in the calculation of $P(D=D_I|N)$, i.e. set to 1. In other examples, this term may be calculated and taken into account in the calculation of $P(D=D_I|N)$. For example, in the case of gender, where the non-image patient data N includes a gender of male, the marginal likelihood may be taken as 0.5 (e.g. on the basis that there are an equal number of male and female patients).

In some examples, an approximation may be made that every medical abnormality has an equal probability of occurring. Under this approximation, the second probability $P(D=D_I)$ referred to above is the same in the calculation for all candidate images I and the medical abnormality indicated thereby. Under this approximation, this term can be ignored for the purposes of determining a relative score for each of the candidate images I.

In other examples, individual second probabilities $P(D=D_I)$ may be determined for different ones of the medical abnormalities. For example, the method may include determining the second probability $P(D=D_I)$ based on a ratio of the number $N_D$ of candidate images in the database that show the medical abnormality ($D_I$) known to be indicated by the candidate image (I) to the total number N of candidate images in the database. For example, the second probability $P(D=D_I)$ may be calculated using the formula $P(D=D_I)=N_D/N_T$, where $N_D$ is the number of candidate images in the database indicating the medical abnormality D, and $N_T$ is the total number of images in the database. This may help provide that candidate images I indicating more common medical abnormalities (and hence which may have a higher probability of being relevant to any given query image Q) have a higher first probability $P(D=D_I|N)$, and hence may be more likely to be retrieved as relevant images.

The first likelihood $P(N|D=D_I)$ (i.e. the likelihood of observing the non-image patient data N given the medical abnormality $D_I$ known to be indicated by the candidate image I) may be determined from distribution data representing a distribution of the medical abnormality $D_I$ known to be indicated by the candidate image I among said non-image patient data of a population of patients. These distributions may be derived empirically. This may help provide that candidate images I indicating medical abnormalities that have a higher likelihood of occurring for the specific non-image patient data N associated with the query image Q (and hence which may have a higher probability of being relevant to that query image Q) have a higher first probability $P(D=D_I|N)$, and hence may be more likely to be retrieved as relevant images.

Figure 2:
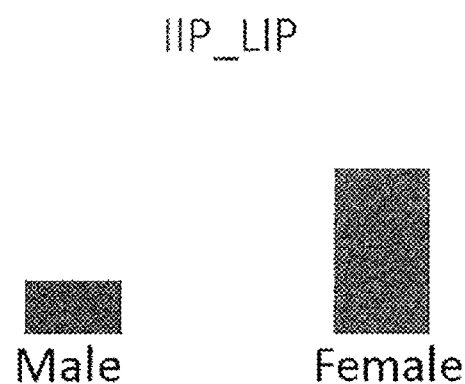
FIG. 2 is a graph illustrating schematically a distribution of a disease across gender, according to an example.

In some examples, the distributions may be binomial, such as for age (i.e. male and female) or smoking status (i.e. smoker and non-smoker). For example, referring briefly to FIG. 2, there is illustrated schematically the distribution of Idiopathic Interstitial Pneumonia, specifically Lymphocytic Interstitial Pneumonia (IIP_LIP) among gender (i.e. male and female). As shown in the Figure, prevalence of this disease in females is three times that in males.

Figure 3:
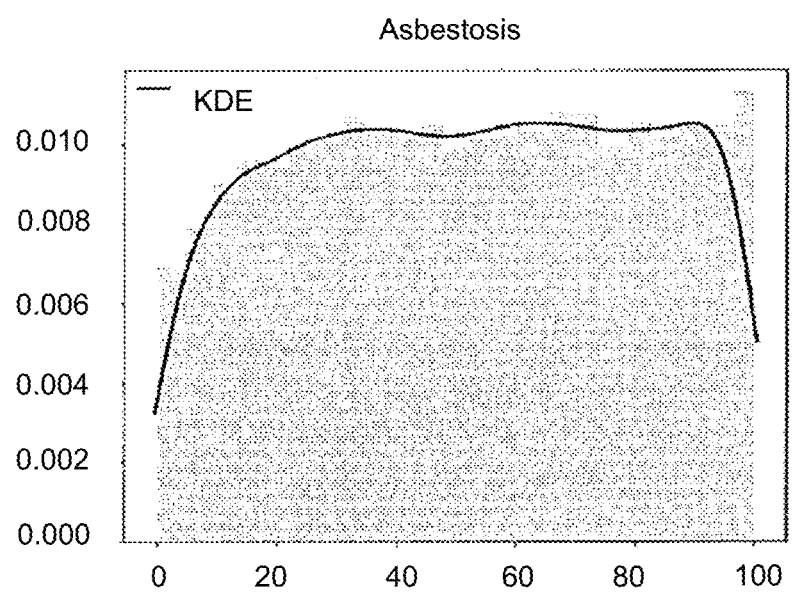
FIG. 3 is a graph illustrating schematically a distribution of a disease across age, according to an example.

In some examples, the distributions may be continuous or quasi continuous, such as for age (e.g. distribution over age in years of the patients). For example, referring briefly to FIG. 3, there is illustrated schematically the distribution of Kernel Density Estimation (KDE), i.e. a measure of disease likelihood, for Asbestosis among ages 1 to 100. The bars illustrate the asbestosis disease likelihood for each age bracket (e.g. in 4-year groupings), and the line illustrates an estimate of the continuous distribution of KDE for asbestosis among age.

In some examples, the distribution may be derived from a cohort of patient information, for example the patient information stored in association with the candidate images I in the database. For example, for each of a plurality of medical abnormalities, patient records where the medical abnormality has been recorded may be extracted, and the distribution of the medical abnormality among particular classifications or types of non-image patient data may be determined. For example, the non-image patient data may be gender, and the distribution of each medical abnormality among males and females may be determined. As another example, the non-image patient data may be age, and the distribution of each medical abnormality across different ages may be determined.

In some examples, the distribution may be determined from empirical studies, for example as published in medical journals or text books. In some examples, the distribution may be determined by consolidating empirical distribution information from a plurality of sources, for example from medical articles. In some examples, the distribution may be available in structured form from a third party, and the distribution may be obtained from a third party, such as a medical publisher.

In some examples, for example where no empirical data exists or is available, the distributions may be determined by a medical expert or a group of medical experts. For example, in the case of binomial distributions such as gender or smoking status, a medical expert or group of medical experts may provide, based on their knowledge and experience, probabilities of the prevalence of a given medical abnormality among certain demographics, such as among males and females, and/or among smokers and non-smokers. In the case of continuous or quasi continuous distributions such as age, the distribution may be derived from a medical expert, or a group of medical experts, adjusting an editable graph to recreate, according to their knowledge and experience, a continuous distribution of the medical abnormality among the non-image patient data, such as across age ranges.

An example calculation of the first probability $P(D=D_I|N)$ for three different candidate images 1, 2, 3 is given for illustrative purposes. Each candidate image indicates a different disease D1, D2, D3, respectively. In this example, the non-image patient data N of the query image Q indicates that the patient is a female. The distribution of the diseases D1, D2, and D3 across gender (e.g. empirically derived) is given in the following table.

| Image | Disease | Female | Male |
|---|---|---|---|
| 1 | D1 | 0.2 | 0.8 |
| 2 | D2 | 0.5 | 0.5 |
| 3 | D3 | 0.8 | 0.2 |

The likelihood $P(N|D=D_I)$ of observing the non-image patient data N (i.e. Female) given the disease $D_I$ known to be indicated by the candidate image I is 0.2 for image 1, 0.5 for image 2, and 0.8 for image 3. In this example, it is assumed that the diseases D1, D2, and D3 are equally likely to occur in nature, and hence the second probability $P(D=D_I)$ is ⅓ for each of images 1 to 3. In this example, the marginal likelihood P(N) is 0.5, on the basis that there are an equal number of male and female patients. Accordingly, using equation (1), the first probability $P(D=D_I|N)$ of the medical abnormality D indicated by the query image Q being the medical abnormality $D_I$ known to be indicated by the candidate image I given the non-image patient data N associated with the query image Q, is calculated as per the following table.

| Image | $P(D = D_I|N)$ |
|---|---|
| 1 | 2/15 |
| 2 | 5/15 |
| 3 | 8/15 |

Accordingly, the candidate image (image 3) indicating the medical abnormality (disease 3) with the highest likelihood (0.8) of occurring in Females (i.e. which the non-image patient data N specifies the patient is) has the highest (8/15) first probability $P(D=D_I|N)$. On the other hand, the candidate image (image 1) indicating the medical abnormality (disease 1) with the lowest likelihood (0.2) of occurring in Females (i.e. which the non-image patient data N specifies the patient is) has the lowest (2/15) first probability $P(D=D_I|N)$. Basing retrieval of the candidate images additionally on the first probability may therefore help to improve the chance that the medical abnormality indicated in the candidate image is the same as that of the query image, and hence improve the relevance of the retrieved candidate images I to the query image Q.

As mentioned, in step 110, the method includes determining, for each of the plurality of candidate images I, based on the determined similarity metric and the determined first probability $P(D=D_I|N)$, a score S.

In some examples, the score may be a simple addition or other combination of the similarity metric and the determined first probability $P(D=D_I|N)$. For example, the score may be based on the addition of a similarity metric based on the reciprocal of the distance between the query and candidate image descriptors, and the first probability $P(D=D_I|N)$. In this example, the smaller the distance between the candidate and query image vectors, the larger the score, and the larger the first probability $P(D=D_I|N)$, the larger the score (and vice versa). In some examples, the equation for calculating the score may have an adjustable parameter, for example a parameter by which the first probability $P(D=D_I|N)$ is multiplied. This parameter may be adjusted to affect the degree to which the first probability $P(D=D_I|N)$ influences the score S. The parameter may be user set, for example from experience of the function or effectiveness of the score to retrieve relevant candidate images I.

In some examples, the score S may be determined based on the scoring equation $$S=\|q-i\|^2-\lambda \log(P(D=D_I|N)) \quad (2)$$

where q is the image descriptor of the query image Q, i is the image descriptor of the candidate image I, $\lambda$ is an adjustable parameter, and $P(D=D_I|N)$ is the first probability of the medical abnormality D indicated by the query image Q being the medical abnormality $D_I$ known to be indicated by the candidate image I given the non-image patient data N associated with the query image.

In this example, the smaller the distance between the candidate and query image vectors, the smaller the score, and the larger the first probability $P(D=D_I|N)$, the smaller the score (and vice versa). In this example, a candidate image I with a small score is taken as having a high relevance to the query image Q. The adjustable parameter $\lambda$ may be adjusted to affect the degree to which the first probability $P(D=D_I|N)$ influences the score S. The parameter may be user set, for example from experience of the function or effectiveness of the score to retrieve relevant candidate images I.

The scoring equation (2) results from the application of a Bayes framework to combine evidence from image descriptors and non-image patient data. The derivation of equation (2) using this Bayes framework is described in the following:

According to Bayesian inference, the probability P(I|Q,N) of a candidate image I being relevant given the query image Q and the non-image patient data N can be factorized as:

$$P(I|Q, N) = \frac{P(Q|I, N)P(I|N)}{P(Q|N)} \quad (3)$$

where P(Q|I,N) is the likelihood of observing the query image Q given the candidate image and the non-image patient data N, P(I|N) is an estimate of the probability of the candidate image I occurring given the non-image patient data N, and P(Q|N) is the marginal likelihood of observing the query image Q given the non-image patient data N.

The denominator P(Q|N) is the same for all candidate images I and hence does not affect a relative scoring of the candidate images I, and hence is ignored (e.g. set to 1).

Regarding the P(Q|I,N) term of equation (3), in order to make equation (3) tractable, the naive Bayes assumption is used, which sets:

$$P(Q|I,N) \stackrel{\text{def}}{=} P(Q|I) \quad (4).$$

Further, the normal distribution assumption is used, which sets:

$$P(Q|I) \stackrel{\text{def}}{=} \left(\frac{1}{\sqrt{2\pi\sigma^2}}\right) e^{\left(-\frac{\|q-i\|^2}{2\sigma^2}\right)} \quad (5)$$

where q is the image descriptor of the query image Q, i is the image descriptor of the candidate image I, and σ is a fixed covariance parameter. In other words, the likelihood of observing a query image Q given a candidate image I is defined as a normal distribution centered on the candidate image descriptor i.

Regarding the P(I|N) term of equation (3), this can be further decomposed:

$$P(I|N) = \Sigma P(I|D) P(D|N) \quad (6)$$

However, the medical abnormality D is known for each candidate image I Therefore, P(I|D) is only non-zero in the case where D=$D_I$. Further, it is assumed that all images I given a particular medical abnormality are equally likely. Accordingly, equation (6) can be re-written as:

$$P(I|N) = \frac{1}{N_D} P(D = D_I | N) \quad (7)$$

where $N_D$ is the total number of images of the medical abnormality D in the database.

To determine the first probability P(D=$D_I$|N) of the medical abnormality D indicated by the query image Q being the medical abnormality $D_I$ known to be indicated by the candidate image I given the non-image patient data N associated with the query image Q, Bayesian inference may be applied:

$$P(D = D_I | N) = \frac{P(N | D = D_I) P(D = D_I)}{P(N)} \quad (8)$$

Equation (8) is the same as equation (1) described above, and the first probability P(D=$D_I$|N) can be calculated as described above. It is noted that in cases where P(D=$D_I$) is calculated as $N_D$/N as described above, this $N_D$ cancels with that of equation (7).

Inserting equations (5), (4), and (7) and (8) into equation (3) returns:

$$P(I|Q,N) = P(D = D_I | N) \left(\frac{1}{\sqrt{2\pi\sigma^2}}\right) e^{\left(-\frac{\|q-i\|^2}{2\sigma^2}\right)} \quad (9)$$

The objective is to determine a relative score S for each candidate image I rather than the probability P(I|Q,N). Taking the natural logarithm of equation (9) will not change the order or ranking of the scores S. Further, equation (9) can be negated to score images in ascending order of relevance. Further, the covariance parameter σ terms can be replaced by an overall adjustable parameter λ because both are constants. Applying these operations, equation (9) becomes a scoring equation that can be written as:

$$S = \|q-i\|^2 - \lambda \log(P(D=D_I|N)) \quad (10)$$

Note that equation (10) is the same as equation (2). Accordingly, if a previous image retrieval technique were based on a score function based only on the distance between image descriptors of the query image and candidate image, then equation (2)/(10) would update that score function with scaled non-image patient data log probability. Accordingly, the non-image patient data N may be effectively incorporated into candidate image retrieval. The use of the Bayesian framework allows a mathematically proper definition of a score function that takes into account both image and non-image data.

In some examples, the score, which is based on both the similarity metric (i.e. representative of visual similarity) and on the first probability (i.e. representative of the effect of the non-image patient data), may alternatively or additionally be expressed explicitly as the constituent parts, i.e. the similarity metric part and the first probability part. This may allow for tractability of the score, i.e. allow a user or administrator to inspect why a particular candidate image I has been given a particular score (e.g. due to the visual similarity, the first probability, or a mixture of both). This may provide for improved tractability, transparency and/or usability, for example as compared to a 'black box' type system where such a decomposition is not possible or less readily available.

As mentioned, the method includes, in step 112, retrieving one or more of the candidate images I from the database in accordance with the determined scores.

In some examples, the method may include ranking the candidate images I in order of the determined score S; and retrieving the one or more candidate images I from the database may be based on the ranking. For example, in cases where a low score indicates high relevance (such as with scoring function of equation (2)) the candidate images I may be ranked in order of increasing score (such that a low score has a high rank), and only those candidate images I having a rank higher than a predetermined rank may be retrieved from the database. For example, only those candidate images with a score in the lowest 10 scores may be retrieved from the database. As another example, in cases where a high score indicates high relevance (such as where the similarity metric and the first probability are added together) the candidate images I may be ranked in order of decreasing score (such that a high score has a high rank), and only those candidate images I having a rank higher than a predetermined rank may be retrieved from the database. For example, only those candidate images with a score in the highest 10 scores may be retrieved from the database.

In some examples, the method may include determining which candidate images I have a score above a predetermined threshold, and retrieving only those candidate images I with a score above the predetermined threshold from the database.

In some examples, the method may include retrieving (only) the candidate image I having the highest (in examples where a high score indicates high relevance) or lowest (in examples where a low score indicated high relevance) score. In this way, only the most relevant image may be retrieved.

Retrieving candidate image(s) based the determined score may allow for only those candidate images I that are relevant to the query image Q to be retrieved from the database, which may provide a more efficient resources for example as compared to retrieving all of the candidate images I from the database. Further, incorporation of the non-image patient data N into the determination of the score may provide that the retrieved images are more relevant to a given query image Q for example as compared to if only visual similarity were used for the score.

In some examples, the method may include outputting the retrieved candidate images I for display on a display device. For example, the retrieved candidate images I may be rendered on a computer monitor or other display screen. The retrieved candidate images I may each be output for display in association with data (such as text) indicating the medical abnormality D known to be indicated in the candidate image I. The radiologist or other medical professional may compare the query image Q with the output candidate image or images I for which the medical abnormality D is known. This may assist the radiologist or other medical professional to determine or diagnose the medical abnormality indicated in the query image Q. Incorporation of the non-image patient data N into the determination of the score may provide that the retrieved and accordingly displayed images are more relevant to a given query image Q for example as compared to if only visual similarity were used for the score. Since the displayed images I are more relevant to the query image (i.e. a more likely to indicate the medical abnormality indicated in the query image Q) the medical professional may more efficiently and effectively determine or diagnose the medical abnormality in the query image.

The candidate images I, along with their associated medical abnormality data, being retrieved based on the score determined based on both the similarity metric and the first probability may allow to narrow a list of medical abnormalities that the medical professional need consider as a diagnosis for the medical abnormality indicated in the query image Q, for example as compared to if the score was based on the similarity metric alone.

Figure 4:
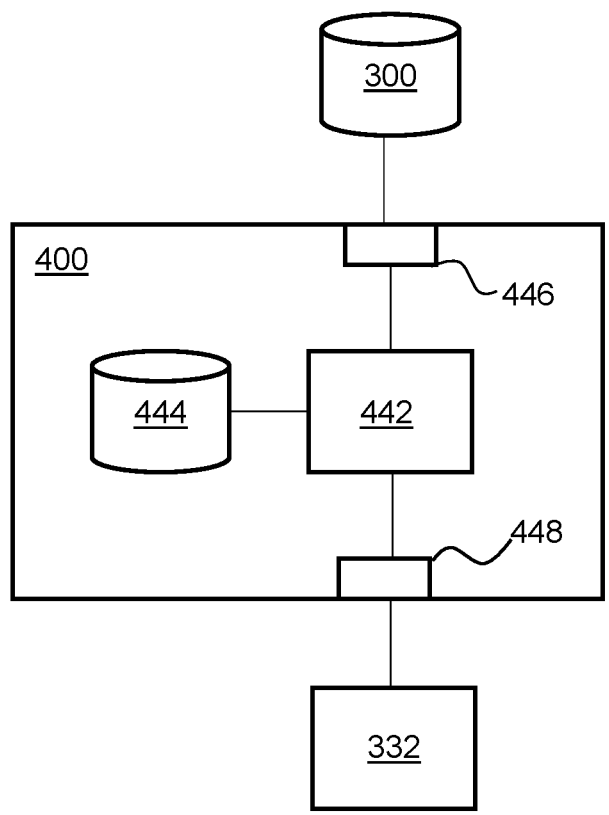
FIG. 4 is a diagram illustrating schematically an apparatus according to an example.

Referring to FIG. 4, there is illustrated an example apparatus 400. For example, the apparatus 400 may be a computer. The apparatus 400 may be configured to perform the method described with reference to FIGS. 1 to 3. The apparatus 400 includes a processor 442 in communication with a non-transitory memory device 444. The processor 442 may be configured to execute the method described with reference to FIGS. 1 to 3. The non-transitory memory device 444 may store a computer program which when executed by the processor 442 causes the processor 442 to perform any of the example methods described with reference to FIGS. 1 to 3. In some examples, the computer program may be provided on one or more non-transitory computer readable media.

In this example, the apparatus 400 includes a first interface 446 and a second interface 448. The first interface 446 is configured to communicate with a database 300. The communication may be via wired or wireless communication channels. The database 300 may store the candidate images I, the medical abnormality data associated with each candidate image I, and the image descriptor associated with each candidate image I, for example as described above. The first interface 446 may be configured to receive (for example as a result of a request from the apparatus 400), for each of a plurality of candidate images I stored in a database 300 (for example for all of the candidate images I stored in the database 300) the image descriptor of the candidate image I and medical abnormality data indicating the medical abnormality $D_I$ known to be indicated by the candidate image I. The first interface 446 may also receive the one or more candidate images I retrieved from the database 300 (e.g. requested to be retrieved from the database by the processor 442) in accordance with the determined scores.

The second interface 448 is configured to communicate with a user interface device 332. For example, the user interface device 332 may include a display device such as a computer monitor, and/or a user input device such as a keyboard and mouse and/or a touch screen, or the like.

The second interface 448 may be configured to receive the query image Q, or the image descriptor of a query image Q, and the non-image patient data N associated with the query image Q, from the user interface device 448. For example, the medical practitioner may specify the query image Q and the non-image patient data N associated with the query image using the user interface device 332, and this may be communicated to the second interface 448. As mentioned, in some examples, the processor 442 may apply encoding to the query image to determine the query image descriptor. In other examples, the query image descriptor may be pre-calculated and communicated to the processor along with the non-image patient data N.

The second interface 448 may be configured to output the retrieved candidate images I, and the medical abnormality data associated with those retrieved candidate images, to the user interface device 332. For example, the second interface 448 may output the retrieved candidate images I for display on the display device of the user interface device 332, for example in association with the medical abnormality data associated with each of the retrieved candidate images I.

Similarly to as described above, the apparatus 400 allows for retrieval and for example display of candidate images I that are more relevant to a query image Q (i.e. a more likely to indicate the medical abnormality indicated in the query image Q) for example as compared to retrieval based on visual similarity alone.

The apparatus 400 and method described above may allow for a medical professional to more efficiently and effectively determine or diagnose the medical abnormality in the query image Q. Moreover, the improved relevance of the retrieved images I is provided for by incorporating into the score the first probability $P(D=D_I|N)$ which encapsulates the natural phenomenon of certain medical abnormalities such as diseases being linked to (i.e. having particular prevalence in) certain non-image patient data such as age, gender, and the like. For example, the first probability $P(D=D_I|N)$ can be based on real-world and/or empirical observations of medical abnormality prevalence given non-image patient data. The improved relevance of the retrieved candidate images I is therefore based on an encapsulation of natural phenomena occurring in the medical field, therefore providing an objective basis on which the relevance is improved.

The above examples are to be understood as illustrative examples of the invention. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

What is claimed is:

1. A computer implemented image retrieval method comprising:
   receiving an image descriptor of a query image and non-image patient data associated with the query image, the query image indicating a medical abnormality;
   receiving, for each of a plurality of candidate images stored in a database, an image descriptor of the candidate image and medical abnormality data indicating a medical abnormality known to be indicated by the candidate image;
   determining, for each of the plurality of candidate images, a similarity metric representing a similarity between the image descriptor of the query image and the image descriptor of the candidate image;
   determining, for each of the plurality of candidate images, a first probability of the medical abnormality indicated by the query image being the medical abnormality known to be indicated by the candidate image given the non-image patient data associated with the query image, wherein the non-image patient data is derived from header information of the query image;
   determining, for each of the plurality of candidate images, a relevance score based on the similarity metric and a logarithmic function of the first probability; and
   retrieving one or more of the plurality of candidate images from the database in accordance with the relevance score.

2. The method of claim 1 wherein determining the first probability comprises determining the first probability using Bayesian inference.

3. The method of claim 1 wherein determining the first probability comprises determining the first probability based on a first likelihood of observing the non-image patient data given the medical abnormality known to be indicated by the candidate image.

4. The method of claim 3 further comprises determining the first likelihood from first distribution data representing a first distribution of the medical abnormality known to be indicated by the candidate image among the non-image patient data of a population of patients.

5. The method of claim 4 further comprises deriving the first distribution empirically.

6. The method of claim 1 wherein the non-image patient data comprises demographic data, clinical data or a combination thereof.

7. The method of claim 1 wherein determining the first probability comprises determining the first probability based on a second probability of an occurrence of the medical abnormality known to be indicated by the candidate image among medical abnormalities.

8. The method of claim 7 further comprising determining the second probability based on a ratio of a number of candidate images in the database that show the medical abnormality known to be indicated by the candidate image to a total number of candidate images in the database.

9. The method of claim 1 wherein determining the first probability $P(D=D_I|N)$ comprises determining the first probability using an equation:

$$P(D = D_I | N) = \frac{P(N | D = D_I)P(D = D_I)}{P(N)}$$

where $P(N|D=D_I)$ is a first likelihood of observing the non-image patient data N given the medical abnormality $D_I$ known to be indicated by the candidate image I, $P(D=D_I)$ is a second probability of an occurrence of the medical abnormality $D_I$ known to be indicated by the candidate image I among medical abnormalities, and $P(N)$ is a marginal likelihood of observing the non-image patient data N among other non-image patient data.

10. The method of claim 1 wherein the similarity metric comprises a distance in a vector space between the image descriptor of the query image and the image descriptor of the candidate image.

11. The method of claim 1 wherein determining the relevance score comprises determining the relevance score based on a scoring equation:

$$S=\|q-i\|^2 \lambda \log(P(D=D_I|N))$$

where S is the relevance score, q is the image descriptor of the query image, i is the image descriptor of the candidate image, $\lambda$ is an adjustable parameter, and $P(D=D_I|N)$ is the first probability of the medical abnormality D indicated by the query image being the medical abnormality $D_I$ known to be indicated by the candidate image given the non-image patient data N associated with the query image.

12. The method of claim 1 further comprising outputting the retrieved candidate images for display on a display device.

13. The method of claim 1 further comprising displaying the retrieved candidate images on a display device in accordance with the determined relevance scores.

14. An apparatus for image retrieval, comprising:
   a non-transitory memory device for storing a computer program; and
   a processor in communication with the memory device, the processor being operative with the computer program to perform steps including
      determining, for at least one of a plurality of candidate images, a similarity metric representing a similarity between an image descriptor of a query image and an image descriptor of the candidate image,
      determining, for the at least one of the plurality of candidate images, a first probability of a medical abnormality indicated by the query image being a medical abnormality known to be indicated by the candidate image given non-image patient data associated with the query image, wherein the non-image patient data is derived from header information of the query image,
      determining, for the at least one of the plurality of candidate images, a relevance score based on the similarity metric and a logarithmic function of the first probability, and
      retrieving one or more of the plurality of candidate images from a database in accordance with the relevance score.

15. The apparatus of claim 14 wherein the processor is operative with the computer program to determine the first probability by determining the first probability based on a first likelihood of observing the non-image patient data given the medical abnormality known to be indicated by the candidate image.

16. The apparatus of claim 15 wherein the processor is operative with the computer program to determine the first likelihood from first distribution data representing a first distribution of the medical abnormality known to be indicated by the candidate image among the non-image patient data of a population of patients.

17. The apparatus of claim 14 wherein the processor is operative with the computer program to determine the first probability by determining the first probability based on a second probability of an occurrence of the medical abnormality known to be indicated by the candidate image among medical abnormalities.

18. The apparatus of claim 17 wherein the processor is operative with the computer program to determine the second probability based on a ratio of a number of candidate images in the database that show the medical abnormality known to be indicated by the candidate image to a total number of candidate images in the database.

19. The apparatus of claim 14 wherein the similarity metric comprises a distance in a vector space between the image descriptor of the query image and the image descriptor of the candidate image.

20. One or more non-transitory computer readable media embodying instructions executable by a computer to perform operations for image retrieval comprising:

determining, for at least one of a plurality of candidate images, a similarity metric representing a similarity between an image descriptor of a query image and an image descriptor of the candidate image;

determining, for the at least one of the plurality of candidate images, a first probability of a medical abnormality indicated by the query image being a medical abnormality known to be indicated by the candidate image given non-image patient data associated with the query image, wherein the non-image patient data is derived from header information of the query image;

determining, for the at least one of the plurality of candidate images, a relevance score based on the similarity metric and a logarithmic function of the first probability; and retrieving one or more of the plurality of candidate images from a database in accordance with the relevance score.

* * * * *